United States Patent

Froggatt

[11] 4,084,094
[45] Apr. 11, 1978

[54] RADIOGRAPHIC APPARATUS

[75] Inventor: Robert Justin Froggatt, Southall, England

[73] Assignee: EMI Limited, Middlesex, England

[21] Appl. No.: 698,225

[22] Filed: Jun. 21, 1976

[30] Foreign Application Priority Data

Jul. 11, 1975 United Kingdom ............... 29184/75

[51] Int. Cl.² ............................................. G03B 41/16
[52] U.S. Cl. ................................ 250/445 T; 250/360
[58] Field of Search ............... 250/439 R, 444, 445 R, 250/445 T, 446, 447, 448, 449, 450, 490, 523, 358 R, 359, 360

[56] References Cited

U.S. PATENT DOCUMENTS

| | | | |
|---|---|---|---|
| 3,106,640 | 10/1963 | Oldendorf | 250/445 T |
| 3,778,614 | 12/1973 | Hounsfield | 250/445 T |

*Primary Examiner*—Craig E. Church
*Attorney, Agent, or Firm*—Cooper, Dunham, Clark, Griffin & Moran

[57] ABSTRACT

In a scanning radiographic apparatus, of a type which is particularly suitable for examining inanimate objects, a fixed source and detectors irradiate an object to be examined along a plurality of beam paths. The object is moved in relation to the source and detectors to direct the radiation along a sufficient number of beam paths to allow suitable processing. The object is, for that purpose, mounted on a turntable which can also execute a reciprocating lateral motion relative to the source and detectors.

4 Claims, 1 Drawing Figure

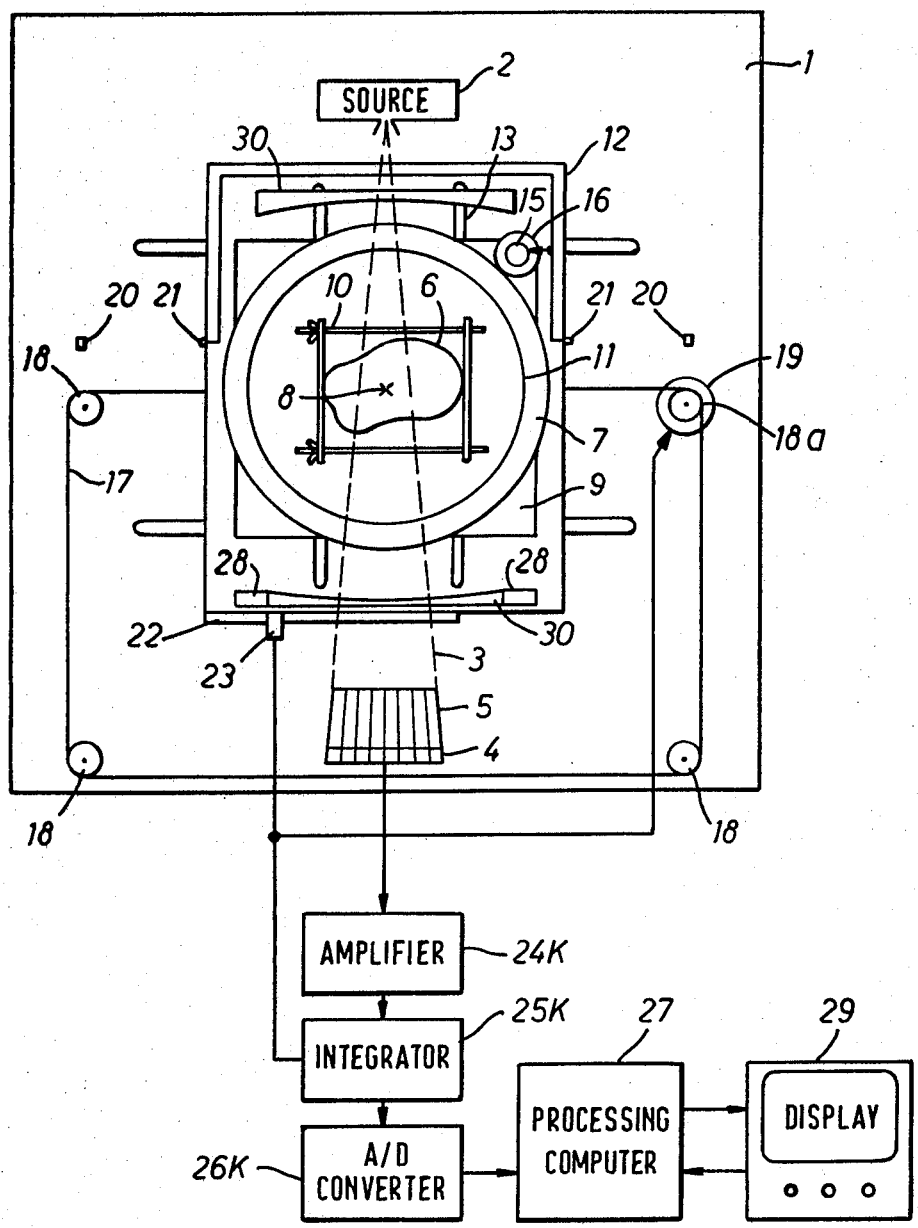

RADIOGRAPHIC APPARATUS

The present invention relates to radiographic apparatus of the kind arranged to provide a representation of the variation of absorption with position across a planar slice of an object with respect to penetrating radiation such as X- or γ- radiation.

In U.S. Pat. No. 3,778,614 there is described apparatus of that type, which includes a source of penetrating radiation and detector means responsive to the radiation. In one embodiment of that apparatus, the source and detector means are reciprocated in the plane of the slice and orbited in steps about a common axis normal to that plane so that the detector means provides output signals indicative of the absorption suffered by the radiation as it traverses many different paths through the body. The processing used is such that the finally displayed distribution of absorption coefficients is the result of successive approximations.

In U.S. Pat. No. 3,946,234 there is described a variation of the apparatus described above, in which a source of radiation is arranged to provide a beam of radiation having a wide angular spread in the plane of the slice. The beam is divided into a plurality of pencil beams by suitable collimators and an array of detectors is provided to measure the intensity of each of these beams after passage through the body. As a result of the large angular spread of these beams the orbital movement can be through relatively larger steps.

The arrangements described in the aforementioned U.S. patents find especial application in diagnostic radiography for medical use, the source and detectors being scanned around a living patient who is maintained in a fixed position. As a result complex arrangements are necessary to provide the necessary electrical, cooling and other connections to the equipment.

In U.S. Pat. No. 3,106,640 there is described an arrangement, for examining a body, having a source of a single beam of radiation and a detector receiving that beam. In some examples of that arrangement, the source and detector are fixed but the body is placed on a turntable for a rotary motion about an axis intersecting the beam and is linearly traversed along a diameter of the turntable. The rotation is relatively fast compared with the traverse so that a great many rotations take place in the time of one traverse. Thus an element of the body on the axis of rotation will substantially remain there during one revolution providing a component to output signals, obtained from the detector during that revolution, which varies slowly. Other elements pass in and out of the beams and provide quickly varying components which can to some extent be removed by a low pass filter. Thus an estimate of absorption for that point is obtained and, in the course of the traverse, data for many such points on a line through the body.

This arrangement could be used for examining inanimate objects and would have the advantage that the source and detector are fixed. However the operation is tedious, the production of information relating to only a single line taking several hours, and the results difficult to interpret in practice. To provide data for a planar section such as that provided by the said U.S. Pat. No. 3,778,614 would require an excessive time for less accurate results.

It is an object of the present invention to provide an alternative arrangement, using a fixed source and detector means, to provide data, capable of analysis by methods such as that disclosed in the said U.S. Pat. No. 3,778,614, in a relatively short period.

According to the invention there is provided an apparatus for examining a planar section of an object by means of penetrating radiation including a source of radiation for irradiating the object, detector means disposed to receive the radiation after passage through the object and provide output signals related to absorption suffered by the radiation during said passage, means arranged to rotate the said object about an axis normal to the said plane to irradiate the object at a plurality of angular positions and means arranged to reciprocate the said axis, in a direction perpendicular to the mean direction of said radiation, to irradiate the body along and provide output signals related to the absorption suffered in passage along at least one set of substantially parallel beam paths therethrough for each of said angular positions.

In order that the invention may be clearly understood and readily carried into effect an example thereof will now be described with reference to the accompanying drawing which shows an apparatus in accordance with the invention.

Referring now to the Figure there is shown mounted in a fixed position on a main frame 1, of the apparatus, a source 2 of a planar fan shaped spread 3 of radiation and a detector means 4. Detector means 4 comprises a plurality of detectors, each arranged to detect the intensity of radiation transmitted along an individual beam in the fan 3, and corresponding collimators 5 to substantially exclude radiation which has not travelled directly from source 2 along the respective path. The source 1 detector means 4 and collimators 5 are essentially the same as those described in U.S. Pat. No. 3,946,234 and the data derived therefrom are processed in essentially the same manner. It should be understood that, if a larger scanning time can be tolerated, source 1 can be arranged to provide a single pencil beam of radiation to be incident on a single detector. In that case the arrangement would be equivalent to one described in one example of the said U.S. Pat. No. 3,778,614.

The apparatus is intended to examine an object 6 which can be placed in the path of the radiation. Scanning motions, equivalent to thoses described in the said U.S. Pat. No. 3,946,234 are provided for the object 6 relative to the fan of radiation 3.

For this purpose the object 6 is mounted on a turntable 7 arranged to rotate, about an axis 8 perpendicular to the plane of the radiation, in a suitable circular track on a plate 9. The object is held in a frame or mount 10 for the purpose of preventing unnecessary movement. This frame may take any convenient form. Also, in this example, the object 6 and frame 10 are surrounded by a water bath 11 having a circular cross section in the plane of the fan of radiation. The water bath 11 may, if the object 6 cannot be readily immersed, omitted or replaced by other means to provide an approximately circular crosssection to an object of irregular shape. If desired object 6 may be placed in a waterproof bag prior to immersion. Alternatively such means for providing a circular cross section may be omitted without excessive detriment to the finally derived representation.

Plate 9 is mounted on a trolley 12 and moves, on bearings (not shown) in tracks 13 on trolley 12, in a direction parallel with the mean direction of X-rays 3.

Trolley 12 also moves, on bearings (not shown) in tracks 14 on main frame 1, in a direction perpendicular to the said mean direction.

Plate 9 carries a stepping motor 15 rotating a gear wheel 16 engaging with gear teeth (not shown) cut into the rim of turntable 7 to provide the circular motion thereof. The motion of plate 9 on trolley 12 is provided by hand, being locked thereafter by conventional means (not shown) although automatic motion may be provided. The motion of trolley 12 on frame 1 is provided by a toothed belt 17 passing around four cog wheels 18 journalled in main frame 1. One gear wheel 18a is driven by a reversible motor 19.

Main frame also carries two stops 20 indicating the extremes of the linear motion of the trolley and the trolley carries two sensors 21 which, as contact with stops 20, provide end of travel signals to motor 15.

Mounted on trolley 12 there is a graticule 22 comprising a transparent substrate having opaque markings thereon. Fixed to main frame 1 is a light source/photocell unit 23 comprising a light source arranged to pass a beam of light through graticule 22 to be intercepted by a photocell. Thus, as successive markings interrupt that light, pulses are produced by unit 23 indicative of the motion of trolley 12. It will be understood that other means may be used to provide such positioning and end stop signals. The signals from unit 23 may also be used to operate motor 15.

In operation the trolley 12 starts at one extreme of its motion and moves steadily to the other extreme scanning the fan of X-rays 3 across the body 6 in a direction perpendicular to its median line. During that scan the output of each detector is applied to a respective amplifier 24 of which 24 k, corresponding to the k th detector, is illustrated. The amplified signal is applied to a respective integrator 25, of which 25 k is shown, where it is integrated for a period determined by pulses from unit 23. Integrator 25 k provides output analogue signals each indicative of the total radiation received during one such period along a beam path, through body 6, defined by the motion of the body relative to the source and the respective detector in that period. The signals are digitised in respective analogue to digital (A/D) converters 26 for provision to a processing computer 27.

Thus in one traverse of trolley 12 carrying body 6 the kth detector provides data for a plurality of beam paths through the body parallel with each other and evenly distributed. Similarly each other detector provides data for a similar parallel set at a different angular orientation in relation to the body, all sets being distributed over a range of angles equal to the angular spread between extreme beams of the fan. At one end or the other of the scan each beam passes through one of two lead blocks 28 to provide an estimate of afterglow in the respective detector.

For the processing used, especially the convolution method described in U.S. Pat. No. 3,924,129 it is desired to provide such parallel sets of data at a great number of angular orientations in the plane being examined. Thus the scan is to be repeated with the body 6 at many orientations relative to the fan of x-rays 3. Thus at the end of the lateral scan a sensor detecting a stop 20 provides an end signal to motor 15 causing it to step through an angle equal to the angular extent of the fan of x-rays 3. Simultaneously motor 19, in response to a signal from unit 23 reverses causing the lateral traverse to be repeated in the opposite direction. It will be apparent that the effective paths through the body examined in the course of repeated traverses with the body at different apparatus of the said U.S. Pat. No. 3,946,234. As in that application the scanning is continued until sets of parallel paths at a sufficient plurality of orientations have been examined. The data are then processed as referred to hereinbefore for viewing on a display unit 29.

It will be apparent that, since the beams of radiation from source 2 are angularly distributed in a fan, the spacing of the beam paths in body 6 is related to its distance from source 2. Thus if the body is closer to the source the beam paths are more closely spaced and resolution is greater. Thus by displacing plate 9 to or from source 1 in tracks 13 the resolution of the final picture can be changed. It should be noted that the extent of the lateral traverse should be sufficient for even the most closely spaced beams to encompass the entire region of interest in the body or should alternatively be variable.

It has been noted that the body 6 should be arranged to have an approximately circular cross section, including any surrounding material. This ensures that its presents approximately the same radiation path length for all scans at different turntable orientations. However such a cross section does not present equal length paths for all positions of the lateral traverse. To provide such equality two saddle shaped members 30 may be mounted on trolley 12. The function of these members is similar to that of the similar members disclosed in U.S. Pat. No. 3,946,234.

What I claim is:

1. An apparatus for examining a planar section of an object by means of penetrating radiation including a source of radiation for irradiating the object, detector means disposed to receive the radiation after passage through the object and provide output signals related to absorption suffered by the radiation during said passage, means arranged to rotate the said object about an axis normal to the said plane to irradiate the object at a plurality of angular positions and means arranged to reciprocate the said axis, in a direction perpendicular to the mean direction of said radiation, to irradiate the body along and provide output signals related to the absorption suffered in passage along at least one set of substantially parallel beam paths therethrough for each of said angular positions.

2. An apparatus according to claim 1 wherein said source is arranged to provide a fan shaped spread of radiation substantially co-planar with said section and said detector means comprises a plurality of detectors disposed to receive radiation transmitted through said object along a plurality of diverging beam paths distributed across said fan to provide, in the course of said reciprocal motion output signals representing the intensity of radiation received along a plurality of substantially parallel beam paths angularly distributed about a respective angular position.

3. An apparatus according to claim 2 including means arranged to move the said axis in a direction parallel with the said mean direction to change the spacing of said diverging beam paths in a region of said object.

4. An apparatus for examining a planar section of an object by means of penetrating radiation including: means disposed outside the object for generating penetrating radiation which propagates substantially along the plane of the slice, traverses the object and emerges therefrom after suffering absorption determined at least in part by the path through the object, said radiation traversing the object at an initial mean angle determined by an initial position of the object relative to the generating means; detecting means sensitive to said radiation and disposed to receive and measure the intensity of radiation which has traversed the object at said initial mean angle; a scanning frame adapted to reciprocate the object in a direction perpendicular to the mean direction of the radiation travelling from the generating means to the detecting means to provide measurements of the intensity of radiation transmitted through the object along at least one set of parallel beam paths disposed at said initial mean angle with respect to the object; a rotary means adapted to rotate said object about an axis, perpendicular to the plane of said section and sharing in the reciprocal motion of the scanning frame, to irradiate the object at a plurality of further mean angles relative thereto and to provide measurements of the intensity of radiation transmitted through the object along further sets of parallel beam paths at said further mean angles; and means for combining the measurements of the intensity of radiation obtained for a plurality of said sets of parallel beam paths to form an image of the said planar section.

* * * * *